United States Patent
Corbin et al.

(10) Patent No.: US 9,181,211 B2
(45) Date of Patent: Nov. 10, 2015

(54) PROCESS FOR THE PRODUCTION OF FURFURAL

(71) Applicant: E I DU PONT DE NEMOURS AND COMPANY, Wilmington, DE (US)

(72) Inventors: David Richard Corbin, West Chester, PA (US); Paul Joseph Fagan, Wilmington, DE (US); Ronnie Ozer, Arden, DE (US); Bhuma Rajagopalan, Wilmington, DE (US); Eric J. Till, Newtown Square, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 13/729,480

(22) Filed: Dec. 28, 2012

(65) Prior Publication Data
US 2013/0172584 A1 Jul. 4, 2013

Related U.S. Application Data

(60) Provisional application No. 61/580,720, filed on Dec. 28, 2011, provisional application No. 61/580,724, filed on Dec. 28, 2011.

(51) Int. Cl.
C07D 311/92 (2006.01)
C07D 307/50 (2006.01)

(52) U.S. Cl.
CPC .................. C07D 307/50 (2013.01)

(58) Field of Classification Search
CPC ............................................... C07D 307/50
USPC ........................................................ 549/489
See application file for complete search history.

(56) References Cited

U.S. PATENT DOCUMENTS

| 2,536,732 A | 1/1951 | Dunlop |
| 2,559,607 A | 7/1951 | Dunning |
| 2,750,394 A | 6/1956 | Peniston |

(Continued)

FOREIGN PATENT DOCUMENTS

| CN | 100999677 A | 7/2007 |
| CN | 101367782 A | 2/2009 |

(Continued)

OTHER PUBLICATIONS

Baerlocher et al., Atlas of Zeolite Framework Types, 6th Revised Edition, Elsevier, Amsterdam, 2007. (Book—Not Included).

(Continued)

*Primary Examiner* — Andrew D Kosar
*Assistant Examiner* — Raymond Covington (57) ABSTRACT

Furfural is produced by mixing an aqueous feedstock solution containing $C_5$ sugar and/or $C_6$ sugar with a heated high boiling, water-miscible solvent, such as sulfolane, and a solid acid catalyst. Furfural product and water can be distilled off, leaving non-volatile solvent behind. Furfural yields of over 70% at as high as 99% conversion have been obtained with this process with sulfolane as the reaction solvent and zeolite beta as the solid acid catalyst. Also, certain by-products (e.g., humins) solubilized in the reaction solvent can be precipitated by addition of water or aqueous feedstock solution and then removed by filtration, thereby providing a convenient and effective way of removing these undesirable byproducts from the reaction mixture.

15 Claims, 2 Drawing Sheets

(56) References Cited

U.S. PATENT DOCUMENTS

| | | | |
|---|---|---|---|
| 4,088,660 | A | 5/1978 | Puurunen |
| 4,154,744 | A | 5/1979 | Hamada |
| 4,366,322 | A | 12/1982 | Raymond |
| 4,503,023 | A | 3/1985 | Breck |
| 4,533,743 | A | 8/1985 | Medeiros |
| 4,897,497 | A | 1/1990 | Fitzpatrick |
| 5,608,105 | A | 3/1997 | Fitzpatrick |
| 5,859,263 | A | 1/1999 | Ghorpade |
| 6,441,202 | B1 | 8/2002 | Lightner |
| 6,518,440 | B2 | 2/2003 | Lightner |
| 6,743,928 | B1 | 6/2004 | Zeitsch |
| 7,572,925 | B2 | 8/2009 | Dumesic |
| 8,277,521 | B2 | 10/2012 | Gruter |
| 8,314,260 | B2 | 11/2012 | Gruter |
| 8,389,749 | B2 | 3/2013 | Dumesic |
| 8,399,688 | B2 | 3/2013 | Dumesic |
| 2003/0032819 | A1 | 2/2003 | Lightner |
| 2007/0298477 | A1 | 12/2007 | Kratochvil |
| 2008/0033187 | A1 | 2/2008 | Zhao |
| 2008/0033188 | A1 | 2/2008 | Dumesic |
| 2009/0124839 | A1 | 5/2009 | Dumesic |
| 2009/0131690 | A1 | 5/2009 | Gruter |
| 2009/0156841 | A1 | 6/2009 | Sanborn |
| 2009/0194407 | A1 | 8/2009 | Tang |
| 2009/0306415 | A1 | 12/2009 | Gruter |
| 2010/0048924 | A1 | 2/2010 | Kilambi |
| 2010/0058650 | A1 | 3/2010 | Gruter |
| 2010/0083565 | A1 | 4/2010 | Gruter |
| 2010/0212218 | A1 | 8/2010 | Gruter |
| 2010/0218415 | A1 | 9/2010 | Gruter |
| 2010/0218416 | A1 | 9/2010 | Gruter |
| 2010/0299991 | A1 | 12/2010 | Gruter |
| 2010/0317879 | A1 | 12/2010 | Zhao |
| 2011/0065159 | A1 | 3/2011 | Raines |
| 2011/0071306 | A1 | 3/2011 | Robinson |
| 2011/0144359 | A1 | 6/2011 | Van Der Heide |
| 2012/0108829 | A1 | 5/2012 | De Jong |
| 2012/0111714 | A1 | 5/2012 | Court |
| 2012/0157697 | A1 | 6/2012 | Burket |
| 2013/0017579 | A1 | 1/2013 | Luterbacher |

FOREIGN PATENT DOCUMENTS

| | | |
|---|---|---|
| CN | 101486695 A | 7/2009 |
| CN | 101130530 A | 11/2010 |
| EP | 2033958 A1 | 3/2009 |
| GB | 799603 A | 8/1958 |
| GB | 838957 A | 6/1960 |
| JP | 02-108682 A | 4/1990 |
| JP | 10265468 A | 10/1998 |
| JP | 2007196174 A | 8/2007 |
| WO | 0047569 A1 | 8/2000 |
| WO | 2009155297 A1 | 12/2009 |
| WO | 2011063500 A1 | 6/2011 |

OTHER PUBLICATIONS

Szostak, Molecular Sieves Principles of Synthesis and Identification, Van Nostrand Reinhold, NY, 1989. (Book—Not Included).
International Search Report, PCT International Application No. PCT/US2012/071992, Mailed April 29, 2013.
Blatter et al., The Preparation of Pure Zeolite Nay and Its Conversion to High-Silica Faujasite, an Experiment for Laboratory Courses in Inorganic Chemistry, J. Chem. Ed., vol. 67, No. 6 (1990), pp. 519-521.
Chen, Hydrophobic Properties of Zeolites, J. Phys. Chem., vol. 80, No. 1 (1976), pp. 60-64.
Dwyer, Zeolite Structure, Composition and Catalysis, Chemistry and Industry (1984), pp. 258-269.
Hutchings et al., Developments in the Production of Methyl Tert-Butyl Ether, Catalysis Today, vol. 15 (1992), pp. 23-49.
Karinen et al., Biorefining: Heterogeneously Catalyzed Reactions of Carbohydrates for the Production of Furfural and Hydroxymethylfurfural, Chem Sus Chem, vol. 4 (2011), pp. 1002-1016.
Agirrezabal-Telleria, et al., Furfural production from xylose using sulfonic ion-exchange resins (Amberlyst) and simultaneous stripping with nitrogen, Bioresource Technology, 2011, 7478-7485, 102.
E. I. Fulmer et al., The Production of Furfural From Xylose Solutions by Means of Hydrochloric Acid-Sodium Chloride Systems, Department of Chemistry, Iowa, Journal of Physical Chemistry, vol. 40 (1936), pp. 133-41.
C. Liu et al., The Enhancement of Xylose Monomer and Xylotriose Degradation by Inorganic Salts in Aqueous Solutions At 180oC, Carbohydrate Research, vol. 341 (2006), pp. 2550-2556.
G. Marcotullio et al., Chloride Ions Enhance Furfural Formation From D-Xylose in Dilute Aqueous Acidic Solutions, Green Chemistry (2010), The Royal Society of Chemistry, pp. 1-8.
F. Tao et al., Efficient Process for the Conversion of Xylose to Furfural With Acidic Ionic Liquid, Can. J. Chem., vol. 89 (2011), pp. 83-87.
Blatter et al., The Preparation of Pure Zeolite Nay and Its Conversion to High-Silican Faujasite, J. Chem Ed., vol. 67 (1990), pp. 519-521.
Hutchings et al., Developments in the Production of Methyl Tert-Butyl Ether, Catalysis Today, vol. 15 (1992) pp. 23-49.
Baerlocher et al., Atlas of Zeolite Framework Types, $6^{th}$ Revised Edition, Elsevier, Amsterdam, 2007 (Book—Not Included).
Karinen et al., Biorefining: Heterogeneously Catalyzed Reactions of Carbohydrates for the Production of Furfural and Hydroxymethylfurfural, Chem Sus Chem, vol. 4 (2011) pp. 1002-1016.
Chen, Hydrophobic Properties of Zeolites, Journal of Physical Chemistry, vol. 80, No. 1 (1976) pp. 60-64.
Dwyer, Zeolite Structure, Composition and Catalysis, Chemistry and Industry, vol. 2 (1984) pp. 258-269.
Szostak, Molecular Seives Principles of Synthesis and Identification, Van Nostr and Reinhold, New York, 1989 (Book—Not Included).
Gairola et al., Hydrothermal Pentose to Furfural Conversion and Simultaneous Extraction With SC-CO2, Kinetics and Application to Biomass Hydrolysates, Bioresource Technology, vol. 123 (2012), pp. 592-598.
Kawamoto et al., Catalytic Pyrolysis of Cellulose in Sulfolane With Some Acidic Catalysts, J Wood Sci, vol. 53 (2007), pp. 127-133.
Suzuki et al., Dehydration of Xylose Over Sulfated Tin Oxide Catalyst: Influences of the Preparation Conditions on the Structural Properties and Catalytic Performance, Applied Catalysis A: General, vol. 408 (2011), pp. 117-124.
Starr et al., High Sulfidity Pulping in Aqueous Sulfolane,Tappi Alkaline Pulping Conference Preprints (1975), pp. 195-198.
Clermont, Delignification of Aspen Wood With Aqueous Sulfolane Solutions, Tappi, vol. 53, No. 12 (1970), pp. 2243-2245.
Chheda et al., Production of 5-Hydroxymethylfufual and furfural by dehydration of biomass-derived mono- and poly-saccharides, Green Chemistry, 2007, 342-350, 9, The Royal Society of Chemistry.
Mamman et al., Furfural: Hemicellulose/xylose-derived biochemical, Biofuels, Bioproducts & Biorefining, 2008, 438-453, Wiley Interscience.
Vazquez et al., Hydrolysis of Sorghum Straw using Phosphoric Acid: Evaluation of Furfural Production, Bioresource Technology, 2007, 3053-3060, 98, Elsevier.
Amiri et al., Production of furans from rice straw by single-phase and biphasic systems, Carbohydrate Research, 2010, 2133-2138, vol. 345.
Weingarten et al., Kinetics of furfural production by dehydration of xylose in a biphasic reactor with microwave heating, Green Chemistry, The Royal Society of Chemistry, 2010, 1423-1429, vol. 12.
Zhao et al., Metal Chlorides in Ionic Liquid Solvents Convert Sugars to 5-Hydroxymethylfurfural, Science, 2007, 1597-1600, vol. 316.
Dias et al., Dehydration of xylose into furfural over micromesoporous sulfonic acid catalysts, Journal of Catalysis, 2005, 414-423, vol. 229.
Orozco, et al., Dilute Acid Hydrolysis of Cellulose and Cellulosic Bio-Waste using a Microwave Reactor System, Sep. 2007, Institute of ChemEng., vol. 85 (B5) pp. 446-449.
US NFOA for U.S. Appl. No. 13/729,526, dated Jun. 19, 2015.

PROCESS FOR THE PRODUCTION OF FURFURAL

This application claims priority under 35 U.S.C. §119(e) from, and claims the benefit of, U.S. Provisional Application No. 61/580,720, filed Dec. 28, 2011; and U.S. Provisional Application No. 61/580,724, filed Dec. 28, 2011; each of which is herein incorporated by reference.

FIELD OF THE INVENTION

A method for the production of furfural from $C_5$ and $C_6$ sugars is provided.

BACKGROUND OF THE INVENTION

Furfural and related compounds are useful precursors and starting materials for industrial chemicals for use as pharmaceuticals, herbicides, stabilizers, and polymers. The current furfural manufacturing process utilizes biomass such as corn cob, sugar cane bagasse, switchgrass or wood waste as a raw material feedstock for obtaining glucose, glucose oligomers, cellulose, xylose, xylose oligomers, arabinose, hemicellulose, and other $C_5$ and $C_6$ sugar monomers, dimers, oligomers, and polymers. The hemicellulose and cellulose are hydrolyzed under acidic conditions to their constituent sugars, such as glucose, xylose, mannose, galactose, rhamnose, and arabinose. Xylose, which is a pentose (i.e., a $C_5$ monosaccharide) is the sugar present in the largest amount in hemicellulose. In a similar aqueous acidic environment, the $C_5$ sugars are subsequently dehydrated and cyclized to furfural. Under similar conditions, $C_6$ sugars can be hydrolyzed and converted in low yields to furfural.

A review by R. Karinen et al. (*ChemSusChem* 4 (2011), pp. 1002-1016) includes several commonly used methods of producing furfural generally as described above. All of the methods involve use of a soluble inorganic acid catalyst, such as sulfuric, phosphoric, or hydrochloric acid. These acids are difficult to separate from the reaction medium or product stream. Low yields can result from formation of undesirable byproducts. Further, their use can require increased capital costs because of associated corrosion and environmental emission issues.

As discussed by Takeshi Suzuki, et al. (Applied Catalysis A: General, 2011, Vol. 408, pp 117-124), solid acid catalysts described in the art require high reaction temperature and pressure and/or supercritical solvent to attain the selective production of furfural with a high yield and a high conversion. The solid acid catalysts are often deactivated by collection of insoluble humins or char on the catalysts.

There remains a need for a process to produce furfural at both high yield and high conversion with a solid acid catalyst, capable of operation in a batch or continuous mode, and which allows for removal of soluble humin byproduct in a batch or continuous mode.

SUMMARY OF THE INVENTION

In an aspect of the invention, there is a process comprising:
(a) providing a reactor comprising a distillation column disposed on top of a reaction vessel, wherein the reaction vessel contains a solid acid catalyst in a water-miscible organic solvent;
(b) bringing an aqueous feedstock solution into contact with the solid acid catalyst in organic solvent in the reaction vessel for a residence time sufficient to produce a mixture of water and furfural, wherein the aqueous feedstock solution comprises $C_5$ sugar, $C_6$ sugar or a mixture thereof, and wherein the contents of the reaction vessel are at a temperature in the range of 100-250° C. and a pressure in the range of 0.0001-0.21 MPa;
(c) removing the mixture of water and furfural from the top of the distillation column; and
(d) adding water or the aqueous feedstock solution to at least a portion of the contents of the reaction vessel comprising organic solvent, water, unreacted sugars and nonvolatile byproducts to precipitate water-insoluble byproducts and removing the precipitated water-insoluble byproducts.

In another aspect, there is a process comprising the steps of:
a) providing a water-miscible organic solvent and a solid acid catalyst in a reaction vessel, wherein the boiling point of the solvent is higher than about 100° C.;
b) providing an aqueous feedstock solution comprising: at least one $C_5$ sugar, at least one $C_6$ sugar, or a mixture of at least one $C_5$ sugar and at least one $C_6$ sugar;
c) adding the feedstock solution to the reaction vessel to form a reaction mixture wherein
  i) the temperature of the reaction mixture is between about 100° C. and about 250° C.,
  ii) the reaction mixture pressure is between 0 MPa and about 0.21 MPa, and
  iii) the feedstock, organic solvent, and catalyst are in contact for a time sufficient to effect a reaction to produce furfural and water;
d) removing vapors of furfural and water from the reaction mixture via reflux through a multistage distillation column;
e) condensing and collecting a solution of furfural and water; and
f) recovering the furfural from the solution of furfural and water collected in step e).

In one embodiment of the invention disclosed herein, the contents of the reaction vessel are heated to a temperature between about 100° C. and about 250° C. before step c).

In another aspect, the process further comprises the steps of:
g) separating the remaining contents, or a portion thereof, of the reaction vessel from the solid acid catalyst;
h) diluting the remaining contents of the reaction vessel, or a portion thereof, in a mixing chamber with water or with an aqueous feedstock solution comprising: at least one $C_5$ sugar, at least one $C_6$ sugar, or a mixture of at least one $C_5$ sugar and at least one $C_6$ sugar, thereby precipitating water-insoluble byproducts;
i) removing the byproducts precipitated in step h), and
j) feeding the solution remaining after step i) back to the reaction vessel.

BRIEF DESCRIPTION OF THE DRAWINGS

Various features and/or embodiments of this invention are illustrated in drawings as described below. These features and/or embodiments are representative only, and the selection of these features and/or embodiments for inclusion in the drawings should not be interpreted as an indication that subject matter not included in the drawings is not suitable for practicing the invention, or that subject matter not included in the drawings is excluded from the scope of the appended claims and equivalents thereof.

DETAILED DESCRIPTION

Definitions

The methods described herein are described with reference to the following terms.

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms; some examples are xylose, arabinose, lyxose and ribose. A hexose is a monosaccharide having six carbon atoms; some examples are glucose and fructose. Disaccharide molecules (e.g., sucrose, lactose, and maltose) consist of two covalently linked monosaccharide units. As used herein, "oligosaccharide" molecules consist of about 3 to about 20 covalently linked monosaccharide units.

As used herein, the term "$C_n$ sugar" includes monosaccharides having n carbon atoms; disaccharides comprising monosaccharide units having n carbon atoms, and oligosaccharides comprising monosaccharide units having n carbon atoms. Thus, "$C_5$ sugar" includes pentoses, disaccharides comprising pentose units, and oligosaccharides comprising pentose units.

As used herein, the term "hemicellulose" refers to a polymer comprising $C_5$ and $C_6$ monosaccharide units. Hemicellulose consists of short, highly branched chains of sugars. In contrast to cellulose, which is a polymer of only glucose, a hemicellulose is a polymer of five different sugars. It contains five-carbon sugars (usually D-xylose and L-arabinose) and six-carbon sugars (D-galactose, D-glucose, and D-mannose). Hemicellulose can also contain uronic acid, sugars in which the terminal carbon's hydroxyl group has been oxidized to a carboxylic acid, such as, D-glucuronic acid, 4-O-methyl-D-glucuronic acid, and D-galacturonic acid. The sugars are partially acetylated. Typically the acetyl content is 1 to 10% by weight of the total weight of the hemicellulose. Xylose is typically the sugar monomer present in hemicellulose in the largest amount.

As used herein, the term "high boiling" denotes a solvent having a boiling point above about 100° C. at 0.101 MPa.

As used herein the term "water-miscible organic solvent" refers to an organic solvent that can form a monophasic solution with water at the temperature at which the reaction is carried out.

As used herein, the term "solid acid catalyst" refers to any solid material containing Brönsted and/or Lewis acid sites, and which is substantially undissolved by the reaction medium under ambient conditions.

As used herein, the term "selectivity" refers to the moles of furfural produced, divided by the moles of xylose transformed to products over a particular time period.

As used herein the term "humin(s)" refers to dark, amorphous byproduct(s) resulting from acid induced sugar and furfural degradation.

Figure 1:
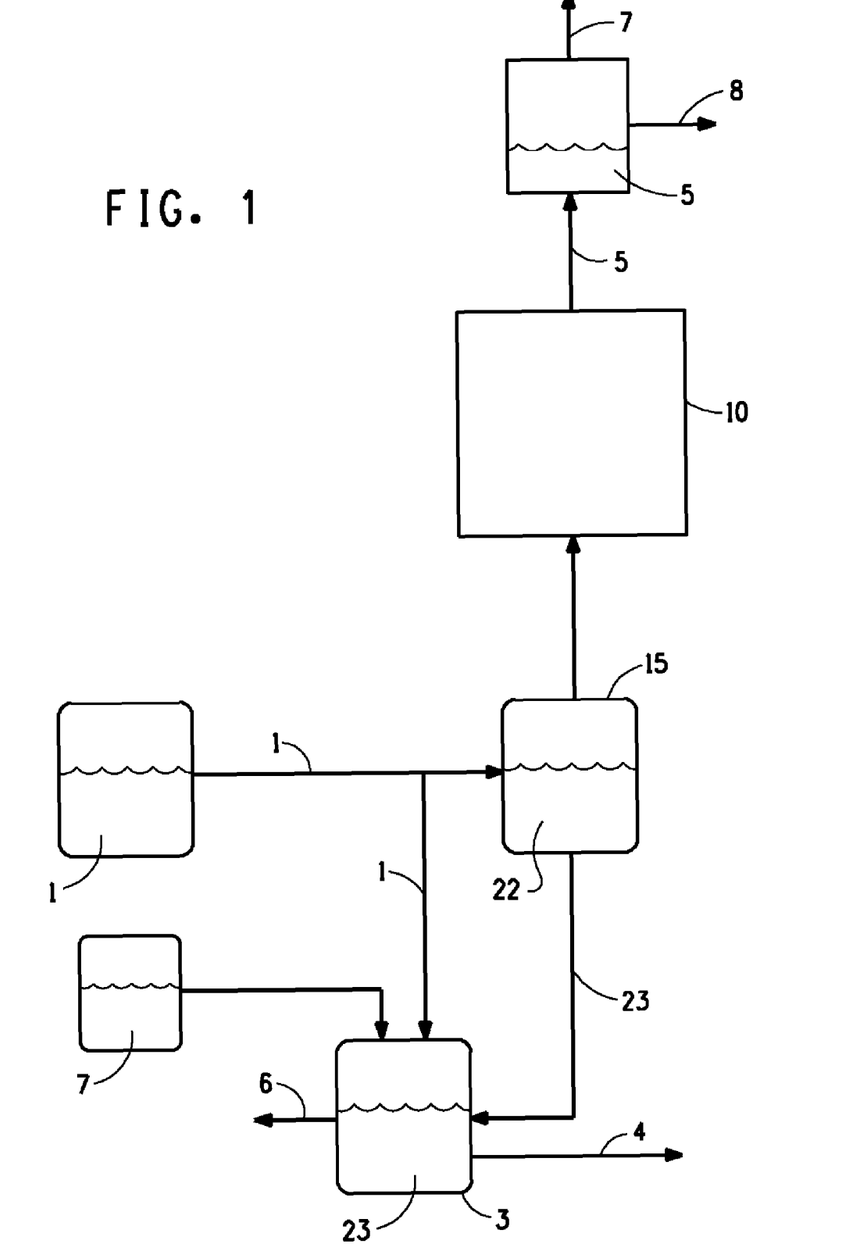
FIG. 1 is a schematic illustration of an exemplary reactor configuration used in the production of furfural in a batch mode, in accordance with various embodiments of the present invention.

In an embodiment, there is a process for the production of furfural comprising providing a reactor configuration comprising a distillation column disposed on top of a reaction vessel, wherein the reaction vessel contains a solid acid catalyst in a water-miscible organic solvent. FIG. 1 shows a schematic illustration of an exemplary reactor configuration comprising a distillation column 10 disposed on top of a reaction vessel 15, wherein the reaction vessel 15 contains a dispersion comprising a solid acid catalyst in a water-miscible organic solvent.

The water-miscible organic solvent has a boiling point higher than about 100° C. at atmospheric pressure. Examples of suitable water-miscible organic solvents include without limitation: sulfolane, polyethylene glycol, isosorbide dimethyl ether, isosorbide, propylene carbonate, poly(ethylene glycol)dimethyl ether, adipic acid, diethylene glycol, 1,3-propanediol, glycerol, gamma-butyrolactone, and gamma-valerolactone.

In one embodiment, the water-miscible organic solvent is sulfolane.

In another embodiment, the water-miscible organic solvent is PEG 4600, PEG 10000, PEG 1000, polyethylene glycol, gamma-valerolactone, gamma-butyrolactone, isosorbide dimethyl ether, propylene carbonate, adipic acid, poly(ethylene glycol)dimethyl ether, isosorbide, Cerenol™ 270 (poly (1,3-propanediol), Cerenol™ 1000 ((poly(1,3-propanediol)), or diethylene glycol.

The solid acid catalyst is a solid acid having the thermal stability required to survive reaction conditions. The solid acid catalyst may be supported on at least one catalyst support. Examples of suitable solid acids include without limitation the following categories: 1) heterogeneous heteropolyacids (HPAs) and their salts, 2) natural or synthetic clay minerals, such as those containing alumina and/or silica (including zeolites), 3) cation exchange resins, 4) metal oxides, 5) mixed metal oxides, 6) metal salts such as metal sulfides, metal sulfates, metal sulfonates, metal nitrates, metal phosphates, metal phosphonates, metal molybdates, metal tungstates, metal borates, and 7) combinations of any members of any of these categories. The metal components of categories 4 to 6 maybe selected from elements from Groups 1 through 12 of the Periodic Table of the Elements, as well as aluminum, chromium, tin, titanium, and zirconium. Examples include, without limitation, sulfated zirconia and sulfated titania.

Suitable HPAs include compounds of the general Formula $X_a M_b O_c^{q-}$ where X is a heteroatom such as phosphorus, silicon, boron, aluminum, germanium, titanium, zirconium, cerium, cobalt or chromium, M is at least one transition metal such as tungsten, molybdenum, niobium, vanadium, or tantalum, and q, a, b, and c are individually selected whole numbers or fractions thereof. Nonlimiting examples of salts of HPAs are lithium, sodium, potassium, cesium, magnesium, barium, copper, gold and gallium, and onium salts such as ammonia. Methods for preparing HPAs are well known in the art and are described, for example, in G. J Hutchings, C. P. Nicolaides and M. S. Scurrel, Catal Today (1994) p 23; selected HPAs are also available commercially, for example, through Sigma-Aldrich Corp. (St. Louis, Mo.). Examples of HPAs suitable for the process of the invention include tungstosilicic acid ($H_4[SiW_{12}O_{40}]^-xH_2O$), tungstophosphoric acid ($H_3[PW_{12}O_{40}]^-xH_2O$), molybdophosphoric acid ($H_3[PMo_{12}O_{40}]^-xH_2O$), molybdosilicic acid ($H_4[SiMo_{12}O_{40}]^-xH_2O$), vanadotungstosilicic acid ($H_{4+n}[SiV_nW_{12-n}O_{40}]^-xH_2O$), vanadotungstophosphoric acid ($H_{3+n}[PV_nW_{12-n}O_{40}]^-xH_2O$), vanadomolybdophosphoric acid ($H_{3+n}[PV_nMo_{12-n}O_{40}]^-xH_2O$), vanadomolybdosilicic acid ($H_{4+n}[SiV_nMo_{12-n}O_{40}]^-xH_2O$), molybdotungstosilicic acid ($H_4[SiMo_nW_{12-n}O_{40}]^-xH_2O$), molybdotungstophosphoric acid ($H_3[PMo_nW_{12-n}O_{40}]^-xH_2O$), wherein n in the Formulas is an integer of 1 to 11 and x is an integer of 1 or more.

Natural clay minerals are well known in the art and include, without limitation, kaolinite, bentonite, attapulgite, montmorillonite and zeolites.

In an embodiment, the solid acid catalyst is a cation exchange resin that is a sulfonic-acid-functionalized polymer. Suitable cation exchange resins include, but are not limited to the following: styrene-divinylbenzene copolymer-based strong cation exchange resins such as Amberlyst® and Dowex® available from Dow Chemicals (Midland, Mich.) (for example, Dowex® Monosphere M-31, Amberlyst® 15, Amberlite® 120), CG resins available from Resintech, Inc. (West Berlin, N.J.), Lewatit resins such as MonoPlus™ S 100H available from Sybron Chemicals, Inc. (Birmingham, N.J.), fluorinated sulfonic acid polymers (these acids are partially or totally fluorinated hydrocarbon polymers containing pendant sulfonic acid groups, which may be partially or totally converted to the salt form) such as Nafion® perfluorinated sulfonic acid polymer, Nafion® Super Acid Catalyst (a bead-form strongly acidic resin which is a copolymer of tetrafluoroethylene and perfluoro-3,6-dioxa-4-methyl-7-octene sulfonyl fluoride, converted to either the proton ($H^+$), or the metal salt form) available from E.I. du Pont de Nemours and Company (Wilmington, Del.).

In an embodiment, the solid acid catalyst is a supported acid catalyst. The support for the solid acid catalyst can be any solid substance that is inert under the reaction conditions including, but not limited to, oxides such as silica, alumina and titania, compounds thereof or combinations thereof; barium sulfate; calcium carbonate; zirconia; carbons, particularly acid washed carbon; and combinations thereof. Acid washed carbon is a carbon that has been washed with an acid, such as nitric acid, sulfuric acid or acetic acid, to remove impurities. The support can be in the form of powder, granules, pellets, or the like. The supported acid catalyst can be prepared by depositing the acid catalyst on the support by any number of methods well known to those skilled in the art of catalysis, such as spraying, soaking or physical mixing, followed by drying, calcination, and if necessary, activation through methods such as reduction or oxidation. The loading of the at least one acid catalyst on the at least one support is from about 0.1-20 weight percent based on the combined weights of the at least one acid catalyst and the at least one support. Certain acid catalysts perform better at low loadings such as 0.1-5%, whereas other acid catalysts are more likely to be useful at higher loadings such as 10-20%. In an embodiment, the acid catalyst is an unsupported catalyst having 100% acid catalyst with no support such as, pure zeolites and acidic ion exchange resins.

Examples of supported solid acid catalysts include, but are not limited to, phosphoric acid on silica, Nafion® perfluorinated sulfonic acid polymer on silica, HPAs on silica, sulfated zirconia, and sulfated titania. In the case of Nafion® on silica, a loading of 12.5% is typical of commercial examples.

In another embodiment, the solid acid catalyst comprises a sulfonic-acid functionalized polymer. In one embodiment, the solid acid catalyst comprises Amberlyst™ 70.

In one embodiment, the solid acid catalyst comprises a Nafion® supported on silica ($SiO_2$).

In one embodiment, the solid acid catalyst comprises natural or synthetic clay minerals, such as those containing alumina and/or silica (including zeolites).

In one embodiment, the solid acid catalyst comprises a zeolite. In one embodiment, the solid acid catalyst is a zeolite comprising zeolite beta, Y zeolite, ZSM-5 zeolite, or Mordenite zeolite or a combination of these.

Zeolites suitable for use herein can be generally represented by the following formula $M_{2/n}O \cdot Al_2O_3 \cdot xSiO_2 \cdot yH_2O$ wherein M is a cation of valence n, x is greater than or equal to about 2, and y is a number determined by the porosity and the hydration state of the zeolite, generally from about 2 to about 8. In naturally occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

The zeolite framework structure has corner-linked tetrahedra with Al or Si atoms at centers of the tetrahedra and oxygen atoms at the corners. Such tetrahedra are combined in a well-defined repeating structure comprising various combinations of 4-, 6-, 8-, 10-, and 12-membered rings. The resulting framework structure is a pore network of regular channels and cages that is useful for separation. Pore dimensions are determined by the geometry of the aluminosilicate tetrahedra forming the zeolite channels or cages, with nominal openings of about 0.26 nm for 6-member rings, about 0.40 nm for 8-member rings, about 0.55 nm for 10-member rings, and about 0.74 nm for 12-member rings (these numbers assume the ionic radii for oxygen). Zeolites with the largest pores, being 8-member rings, 10-member rings, and 12-member rings, are frequently considered small, medium and large pore zeolites, respectively.

In a zeolite, the term "silicon to aluminum ratio" or, equivalently, "Si/Al ratio" means the ratio of silicon atoms to aluminum atoms. Pore dimensions are critical to the performance of these materials in catalytic and separation applications, since this characteristic determines whether molecules of certain size can enter and exit the zeolite framework.

In practice, it has been observed that very slight decreases in ring dimensions can effectively hinder or block movement of particular molecular species through the zeolite structure. The effective pore dimensions that control access to the interior of the zeolites are determined not only by the geometric dimensions of the tetrahedra forming the pore opening, but also by the presence or absence of ions in or near the pore. For example, in the case of zeolite type A, access can be restricted by monovalent ions, such as $Na^+$ or $K^+$, which are situated in or near 8-member ring openings as well as 6-member ring openings. Access can be enhanced by divalent ions, such as $Ca^{2+}$, which are situated only in or near 6-member ring openings. Thus, the potassium and sodium salts of zeolite A exhibit effective pore openings of about 0.3 nm and about 0.4 nm respectively, whereas the calcium salt of zeolite A has an effective pore opening of about 0.5 nm.

The presence or absence of ions in or near the pores, channels and/or cages can also significantly modify the accessible pore volume of the zeolite for sorbing materials. Representative examples of zeolites are (i) small pore zeolites such as NaA (LTA), CaA (LTA), Erionite (ERI), Rho (RHO), ZK-5 (KFI) and chabazite (CHA); (ii) medium pore zeolites such as ZSM-5 (MFI), ZSM-11 (MEL), ZSM-22 (TON), and ZSM-48 (*MRE); and (iii) large pore zeolites such as zeolite beta (BEA), faujasite (FAU), mordenite (MOR), zeolite L (LTL), NaX (FAU), NaY (FAU), DA-Y (FAU) and CaY (FAU). The letters in parentheses give the framework structure type of the zeolite. Definitions of zeolite framework types may be found in the following references: http://www.iza-structure.org/, and Baerlocher, McCusker, Olson ["Atlas of Zeolite Framework Types, $6^{th}$ revised edition, Elsevier, Amsterdam].

Zeolites suitable for use herein include medium or large pore, acidic, hydrophobic zeolites, including without limitation ZSM-5, faujasites, beta, and mordenite zeolites or mixtures thereof, having a high silicon to aluminum ratio in the range of 5:1 to 400:1 or 5:1 to 200:1. Medium pore zeolites have a framework structure consisting of 10-membered rings with a pore size of about 0.5-0.6 nm. Large pore zeolites have a framework structure consisting of 12-membered rings with a pore size of about 0.65 to about 0.75 nm. Hydrophobic zeolites generally have Si/Al ratios greater than or equal to about 5, and the hydrophobicity generally increases with increasing Si/Al ratios. Other suitable zeolites include without limitation acidic large pore zeolites such as H—Y with Si/Al in the range of about 2.25 to 5.

Zeolites with a high Si/Al ratio can be prepared synthetically, or by modification of high alumina containing zeolites using methods known in the art. These methods include without limitation treatment with $SiCl_4$ or $(NH_4)_2SiF_6$ to replace Al with Si, as well as treatment with steam followed by acid. A $SiCl_4$ treatment is described by Blatter [*J. Chem. Ed.* 67 (1990) 519]. A $(NH_4)_2SiF_6$ treatment is described in U.S. Pat. No. 4,503,023. These treatments are generally very effective at increasing the Si/Al ratio for zeolites such as zeolites Y and mordenite.

The presence of aluminum atoms in the frameworks results in hydrophilic sites. On removal of these framework aluminum atoms, water adsorption is seen to decrease and the material becomes more hydrophobic and generally more organophilic. Hydrophobicity in zeolites is further discussed by Chen [*J. Phys. Chem.* 80 (1976) 60]. Generally, high Si/Al containing zeolites exhibit higher thermal and acid stability. Acid forms of zeolites can be prepared by a variety of techniques including ammonium exchange followed by calcination or by direct exchange of alkali ions for protons using mineral acids or ion exchangers. Acid sites in zeolites are further discussed in Dwyer, "Zeolite, Structure, Composition and Catalysis" in *Chemistry and Industry*, Apr. 2, 1984.

Certain types of molecular sieves, of which zeolites are a sub-type, may also be used as the catalytic material in the processes hereof. While zeolites are aluminosilicates, molecular sieves contain other elements in place of aluminum and silicon, but have analogous structures. Large pore, hydrophobic molecular sieves that have similar properties to the preferred zeolites described above are suitable for use herein. Examples of such molecular sieves include without limitation Ti-Beta, B-Beta, and Ga-Beta silicates. Molecular sieves are further discussed in Szostak, *Molecular Sieves Principles of Synthesis and Identification*, (Van Nostrand Reinhold, N.Y., 1989).

The solid acid catalyst is present in the water-miscible organic solvent in the range of 0.01-20 weight % or 0.01-10 weight % or 0.1-5 weight %, based on the total weight of the acid dispersion and water miscible organic solvent. In some embodiments, the acid is present in the solvent at a weight percentage between and optionally including any two of the following values: 0.01, 0.05, 0.10, 0.15, 0.20, 0.50, 1.0, 1.5, 2.0, 3.0, 4.0, 5.0, 6.0, 7.0, 8.0, 9.0, 10, 11, 12, 13, 14, 15, 16, 17, 18, 19, 20 weight percent. The optimal amount of acid catalyst will be affected by what specific solvent is used and is readily determined by one of skill in the art.

The process for the production of furfural also comprises, as shown in the FIG. 1, bringing an aqueous feedstock solution 1 into contact with the solid acid catalyst dispersed in a water miscible organic solvent to form a reaction mixture 22 in the reaction vessel 15 for a residence time sufficient to produce a mixture 5 of water 7 and furfural 8. In an embodiment, the aqueous feedstock solution comprises $C_5$ sugar, $C_6$ sugar or a mixture thereof. In another embodiment, the reaction zone is at a temperature in the range of 100-250° C. and a pressure in the range of 0.0001-0.21 MPa.

The aqueous feedstock comprises at least one $C_5$ sugar, at least one $C_6$ sugar, or a mixture of at least one $C_5$ sugar and at least one $C_6$ sugar. Examples of suitable $C_5$ sugars (pentoses) include without limitation xylose, arabinose, lyxose and ribose. Examples of suitable $C_6$ sugars (hexoses) include without limitation glucose, fructose, mannose, and galactose.

In one embodiment, the aqueous feedstock solution comprises xylose. In other embodiment, the aqueous feedstock solution comprises glucose. In another embodiment, the aqueous feedstock solution comprises xylose and glucose.

The total amount of sugar ($C_5$ sugar, $C_6$ sugar, or a mixture thereof) is present in the aqueous feedstock solution in the range of 0.1-99 weight % or 1-50 weight % or 5-35 weight % or 5-10 weight %, based on the total weight of the aqueous feedstock solution. In some embodiments, the $C_5$ sugar is present in the feedstock solution at a weight percentage between and optionally including any two of the following values: 0.1, 0.5, 1, 2, 3, 4, 5, 6, 7, 8, 9, 10, 15, 17, 19, 21, 23, 25, 30, 35, 40, 45, 50, 55, 60, 65, 70, 75, 80, 85, 90, 95, and 99 weight percent.

The temperature of the reaction mixture 22 is between about 100° C. and about 250° C. or 100-190° C. or 120-180° C. In some embodiments, the temperature of the reaction mixture is between and optionally including any two of the following values: 100, 110, 120, 130, 140, 150, 160, 170, 180, 190, 200, 210, 220, 230, 240, and 250° C. In an embodiment, the contents of the reaction vessel are heated before the step of bringing the aqueous feedstock solution 1 into contact with the solid acid catalyst. In another embodiment, the contents of the reaction vessel are heated after the step of bringing an aqueous feedstock solution 1 into contact with the solid acid catalyst.

The reaction is carried out at a pressure less than about 0.21 MPa, thus eliminating the need for the high-pressure equipment used in some earlier processes. In an embodiment, the reaction mixture 22 and distillation column 10 is kept at a pressure less than 0.21 MPa or less than 0.11 MPa or less than 0.050 MPa.

The process for the production of furfural further comprises, as shown in the FIG. 1, removing the mixture 5 of water 7 and furfural 8 from the top of the distillation column 10. As the reaction proceeds, vapors of furfural 8 and water 7 are removed from the reaction mixture 22 via reflux through a multistage distillation column 10, condensed, and collected as a solution 5 of furfural 8 and water 7. The use of staging in the distillation process allows more efficient stripping of furfural 8 away from the catalyst and minimizes loss of water miscible solvent overhead. This increases furfural yield by driving the reaction toward completion and by minimizing formation of byproducts. Further, because the solid acid catalyst is therefore less likely to suffer deleterious effects of byproduct build-up, the use of multistage distillation in this process increases catalyst lifetime. The use of the water miscible organic solvent also aids in catalysts lifetime by keeping byproducts such as humins dissolved, preventing deposition on the solid catalysts.

The process for the production of furfural further comprises, as shown in the FIG. 1, adding water 7 or the aqueous feedstock solution 1 to at least a portion 23 of the contents of the reaction zone 15 comprising organic solvent, acid catalyst, water, unreacted sugars and nonvolatile byproducts in a mixing zone 3 to precipitate water-insoluble byproducts 4 and removing the precipitated water-insoluble byproducts 4 from the remaining solution 6.

In one embodiment, the process is a batch mode, with reference to FIG. 1, the reaction vessel 15 is charged initially with an acid catalyst and a high boiling, water-miscible solvent and a catalytic amount of solid acid. The contents of the reaction vessel 15 are heated to the reaction temperature. An aqueous feedstock solution 1 containing $C_5$, and/or $C_6$ sugar is added over time to the hot reaction vessel 15. The sugar undergoes chemical transformation to furfural 8, which, along with water 7 from the aqueous feedstock solution 1 and water 7 produced by the reaction, is then removed from the reaction mixture 22 via reflux through a multistage distillation column 10 equipped with a condenser. This minimizes the residence time of furfural 8 in the acidic environment of the reaction mixture 22 and thereby minimizes its degradation. The furfural 8 is separated from the water and purified by any convenient methods known in the art, and the product furfural 8 is isolated. The water is either recycled to the source of the aqueous feedstock solution or is released from the process. After the completion of reaction, non-volatile components are left in the reaction vessel 15 including, but not limited to, the high boiling water-miscible organic solvent, unreacted sugar, unwanted byproducts such as humins, and the solid acid catalyst. The water-insoluble byproducts can be removed by diluting at least a portion 23 of the contents of the reaction vessel with water or an aqueous feedstock solution which results in the precipitation of humins. The ratio of added water or aqueous feedstock solution to reaction vessel contents, referred to herein as the "dilution ratio," can be from about 0.5:1 up to 100:1 by volume. A higher dilution ratio causes more humins to precipitate, and a lower dilution ratio results in less precipitate. In an embodiment, the ratio is from about 3:1 to about 20:1 by volume. In an embodiment, the ratio is from about 1:1 to about 10:1 by volume. In some embodiments, the dilution ratio is between and optionally including any two of the following values: 0.5:1, 1:1, 2:1, 3:1, 4:1, 5:1, 6:1, 7:1, 8:1, 9:1, 10:1, 12:1, 14:1, 16:1, 18:1, 20:1, 25:1, 30:1, 35:1, 40:1, 45:1, 50:1, 55:1, 60:1, 70:1, 80:1, 90:1, and 100:1 by volume. The solution 6 is separated from the humins, and can be recycled into another batch process.

Furfural yields of over 70% at as high as 99% conversion have been obtained with this process with sulfolane as the water miscible organic solvent and zeolite beta as the solid acid catalyst, as shown in Example 1. Also, certain by-products (e.g., humins) solubilized in the reaction solvent can be precipitated by addition of water or aqueous feedstock solution and then removed, thereby providing a convenient and effective way of removing these undesirable byproducts from the reaction mixture.

Figure 2:
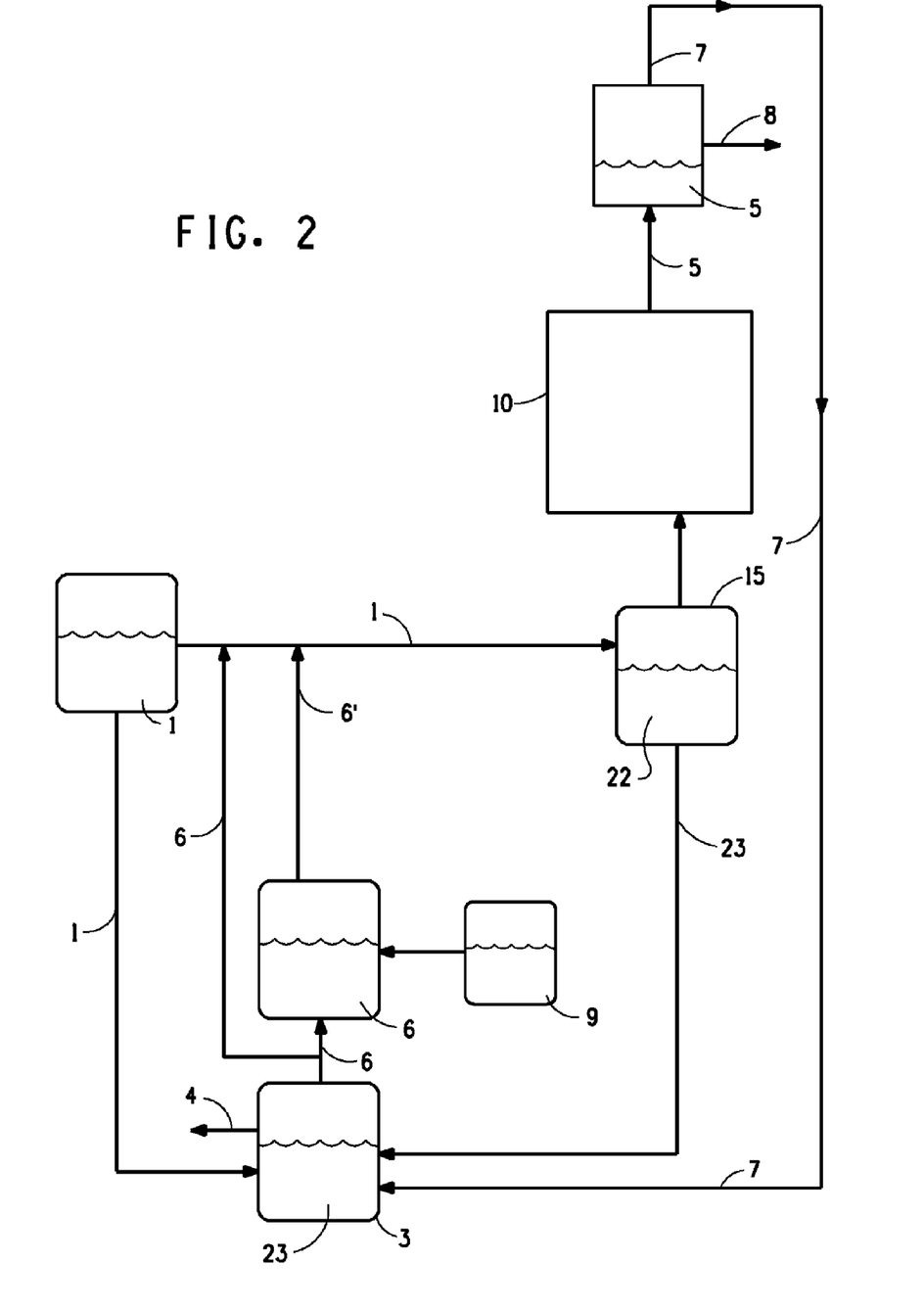
FIG. 2 is a schematic illustration of another exemplary reactor configuration used in the production of furfural in a continuous mode, in accordance with various embodiments of the present invention.

In another embodiment of the process described herein, the process is run continuously. FIG. 2 shows a schematic illustration of another exemplary reactor configuration used in the production of furfural in a continuous mode in accordance with various embodiments of the present invention. With reference to FIG. 2, the reaction vessel 15 is charged initially with a high boiling, polar, water-miscible solvent and solid acid catalyst. The contents of the reaction vessel 15 are heated to the reaction temperature. An aqueous feedstock solution 1 containing $C_5$ and/or $C_6$ sugar solution is added to the hot reaction vessel 15. The sugar undergoes chemical transformation to furfural, which, along with water from the feed and produced by the reaction, is then removed from the reaction mixture 22 via reflux through a multistage distillation column 10 equipped with a condenser. This minimizes the residence time of furfural 8 in the acidic environment and thereby minimizes its degradation. The furfural 8 is separated from the water 7 and purified by any convenient methods known in the art, and the product furfural 8 is isolated. The water 7 is either recycled to the source of the aqueous feedstock solution 1 or can be used in the precipitation of non-volatile reaction by-products or is released from the process.

At least a portion 23 of the contents of the reaction vessel 15 are fed (e.g., pumped), through a filter or screen to prevent aspiration of the solid acid catalyst, and diluted with either aqueous feedstock solution water 1, or water 7 in the mixing zone 3. This initiates precipitation of unwanted byproducts 4, such as humins. The ratio of aqueous sugar solution to reaction vessel contents can be from about 0.5:1 up to 100:1 by volume; in an embodiment, the ratio is from about 3:1 to about 20:1. In an embodiment, the ratio is from about 1:1 to about 10:1 by volume. Any suitable dilution ratio can be used, as described supra. The precipitated byproducts 4 are removed by any convenient means, such as filtration or centrifugation. The isolated solids 4 are conveyed and washed with water 7 or aqueous feedstock solution 1 to reclaim any reaction solvent, furfural or sugar that was retained in the wet solids.

If necessary, the washed solids are then further dried. Isolated solids can be conveyed and burned as an energy source. The precipitate-free liquid 6 can be returned to the source of the aqueous feedstock solution 1 or into the reaction vessel 15. A reservoir of makeup water-miscible organic solvent 9 is available to replace any lost or degraded high boiling solvent. In an embodiment, the precipitate-free liquid 6 is concentrated by evaporation before mixing with water-miscible organic solvent 9 and the resultant mixture 6' is then mixed with the aqueous feedstock stream. The aqueous feedstock solution 1 is finally fed to the reaction vessel 15. The flow of the feedstock 1 can be adjusted partially or completely to go either towards the reactor mixing with 6 or 6', or can be adjusted to go towards 3 mixing with solution 23. Thus, a continuous flow of components into and out of the reaction vessel 15 as well as the other components of the process is established, using the feedstock solution 1 and/or water 7 to precipitate and remove humins 4 from at least a portion 23 of the reaction mixture 22 coming from reaction vessel 15, while simultaneously distilling water and furfural out of reaction vessel 15 into distillation column 10. The flow of liquid and solids as indicated by the arrows in FIG. 2 can occur simultaneously with the proper balance of inlet and outlet flows.

The process described above produces furfural from $C_5$ and/or $C_6$ sugars at both high yield and high conversion, without production of insoluble char in the reaction vessel. In an embodiment, the furfural yield is in the range of or 15-80% or 45-70% or 60-70%. In another embodiment, the conversion is in the range of 30-100 or 80-100 or 90-100%. The disclosed process is capable of operation in a batch or continuous mode. The process can be carried out without the need for high pressure equipment. The use of a solid acid catalyst allows easy separation of products via either flow of liquid or vaporization away from the catalyst. It is also desirable that such a process provide long catalyst life and higher yields than alternative processes. The corrosion and environmental emission issues requiring increased capital costs are avoided. Also, certain by-products (e.g., humins) solubilized in the reaction solvent can be precipitated by addition of water or aqueous feedstock solution and then removed (e.g., by filtration), thereby providing a convenient and effective way of removing these undesirable byproducts from the reaction mixture in both batch and continuous modes of operation. Solid acid catalysts have the advantage of not inducing corrosion in reaction vessels and other process equipment compared to liquid acids. It is also desirable that such a process be carried out without the need for high pressure equipment.

In one embodiment of the invention disclosed herein, a process is provided comprising the steps of:

a) providing a water-miscible organic solvent and a solid acid catalyst in a reaction vessel, wherein the boiling point of the solvent is higher than about 100° C.;

b) providing an aqueous feedstock solution comprising: at least one $C_5$ sugar, at least one $C_6$ sugar, or a mixture of at least one $C_5$ sugar and at least one $C_6$ sugar;

c) adding the feedstock solution to the reaction vessel to form a reaction mixture wherein
  i) the temperature of the reaction mixture is between about 100° C. and about 250° C.,
  ii) the reaction mixture pressure is between 0 MPa and about 0.21 MPa, and
  iii) the feedstock, organic solvent, and catalyst are in contact for a time sufficient to effect a reaction to produce furfural and water;

d) removing vapors of furfural and water from the reaction mixture via reflux through a multistage distillation column;

e) condensing and collecting a solution of furfural and water; and f) recovering the furfural from the solution of furfural and water collected in step e).

In one embodiment of the invention disclosed herein, the contents of the reaction vessel are heated to a temperature between about 100° C. and about 250° C. before step c).

In a further embodiment of the invention disclosed herein, the process further comprises the steps of:

g) separating the remaining contents, or a portion thereof, of the reaction vessel from the solid acid catalyst;

h) diluting the remaining contents of the reaction vessel, or a portion thereof, in a mixing chamber with water or with an aqueous feedstock solution comprising: at least one $C_5$ sugar, at least one $C_6$ sugar, or a mixture of at least one $C_5$ sugar and at least one $C_6$ sugar, thereby precipitating water-insoluble byproducts;

i) removing the byproducts precipitated in step h), and j) feeding the solution remaining after step i) back to the reaction vessel.

The solution remaining after step i) can be concentrated by evaporation before it is fed back to the reaction vessel.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "invention" or "present invention" is a non-limiting term and is not intended to refer to any single variation of the particular invention but encompasses all possible variations described in the specification and recited in the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

Abbreviations

The meaning of abbreviations is as follows: "g" means gram(s), "h" means hour(s), "HPLC" means high pressure liquid chromatography, "m" means meter(s), "min" means minute(s), "mL" means milliliter(s), "mm" means millimeter(s), "MPa" means megapascal(s), "N" means normal, "PTFE" means poly(tetrafluoroethylene), "rpm" means revolutions per minute, and "wt %" means weight percent (age).

Materials

Xylose, sulfolane, and dimethylsulfoxide (DMSO) were obtained from Sigma-Aldrich Corporation (St. Louis, Mo., USA).

The following solid acid catalysts were obtained from Zeolyst International (Conshohocken, Pa.) or Conteka B. V. (now Zeolyst, International): Product #: CBV 400, CBV 500, CBV 712, CBV 720, CBV 760, CBV 780, CP 814C, CP 814E, CP 811B-200, CP 811C-300, CBV 3020, CBV 5020, CBV 1502, CBV 2802 (now CBV 28014), CBV 10A, CBV 20A, and CBV 30A. The solid acid catalyst S-115 (LA) was obtained from Union Carbide Corporation (now UOP, Des Plaines, Ill.). The solid acid catalyst Amberlyst™ 70 was obtained from Dow Chemical Company (Midland, Mich.). Amberlyst™ 70 is a macroreticular polymer based catalyst primarily comprising sulfonic-acid-functionalized styrene divinylbenzene copolymers. The solid acid catalyst 13% Nafion® on silica ($SiO_2$) was obtained from E. I. du Pont de Nemours and Co. (Wilmington, Del.). Nafion® is a registered trademark of E. I. du Pont de Nemours and Company for its perfluorinated sulfonic acid polymer products.

Deionized water was used unless otherwise indicated.

Methods

Distillates and reaction flask contents were analyzed on a calibrated Aminex HPX-87H HPLC column (Bio-Rad Company) using a refractive index detector, and the column wash was analyzed via gas chromatographic analysis using a flame ionization detector and a calibrated 30 m HP-INNOWax GC column (Agilent Technologies).

Example 1

Production of Furfural with Solid Acid Catalysts

Zeolites having different frameworks were used as catalysts as indicated in Table 1, including faujasite (FAU), zeolite beta (BEA), ZSM-5 (MFI), and mordenite (MOR). All zeolites were calcined at 550° C. for 8 h in air prior to use. All of the zeolites are in proton form after calcining except for CBV 10A which was in the sodium form. The polymer catalysts Amberlyst™ 70 and 13% Nafion on silica were used as obtained.

The following amounts and variables were the same for all experiments in this Example: 1) solvent was sulfolane, 2) mass of solvent was 5 g, 3) mass of solid catalyst was 0.075 g (1.5% of the solvent mass), 4) aqueous xylose solution concentration was 5 wt %, 5) xylose solution addition rate was 0.4 mL/min, 6) stirring rate was approximately 500 rpm, 7) reaction run time was 40 min, 8) average reaction temperature was 170° C., 9) oil bath temperature was 250° C., and 10) the internal standard added for analysis was dimethylsulfoxide.

The conversion of xylose to furfural was carried out in a 10 mL three-necked round bottomed flask (Chemglass, Inc. Life Sciences Catalog No. PN CG-1507-03) containing a PTFE-coated stirring bar (VWR Company Catalog No. 58949-010), a thermowell, a threaded adapter with cap (Chemglass, Inc. Life Sciences Catalog No. CG-350-01), and a PTFE-lined silicon septum (National Scientific Catalog No. B7995-15). The flask was connected to a vacuum-jacketed Vigreux distillation column (Chemglass, Inc. Life Sciences Catalog No. CG-1242) loaded with 8.0 g of 4 mm diameter glass beads (Chemglass, Inc. Life Sciences Catalog No. CG-1101-03). The beads were held in place at the bottom of the distillation column with a piece of 1/16" diameter thick fluoropolymer film that was approximately 3/4" wide by 3" long which was either wound up into a coil or folded so that it contained pleats. A 20 mL plastic syringe with Luer lock tip (Chemglass, Inc. Life Sciences Catalog No. PN 309661) was connected to 1/16" fluoropolymer tubing which was pierced through the septum. Addition of the xylose solution from the syringe to the reaction vessel was controlled with a digital syringe pump. The reactions were carried out under an atmosphere of nitrogen.

To the reaction flask were added 5 g of solvent and 0.075 g of solid acid catalyst. The syringe on the syringe pump was filled with an aqueous xylose solution which was weighed prior to addition, and then reweighed after the completion of addition to determine the total amount of xylose solution added to the reaction mixture. After the flask was loaded, it was attached to the distillation column and one end of the 1/16" diameter fluoropolymer tube was attached to the syringe containing the aqueous xylose solution and the other end was inserted through the septum and into the reactor. The flask was lowered into the hot oil to bring the reactor contents to the desired internal temperature and addition of the xylose solution from the syringe using the syringe pump was started. The xylose solution was added at a constant rate and the temperature of the reaction mixture was maintained as constant as possible by slight adjustments to the height of the apparatus in the oil bath. At the end of the reaction, the syringe pump was stopped, the tube was pulled from the reaction flask and the apparatus was raised out of the oil bath.

The amount of distillate collected was weighed, a measured amount of the internal standard (dimethylsulfoxide) was added for analytical purposes, and the solution was then mixed until it was homogeneous (additional water was added to dilute the mixture if necessary). The reaction flask was removed from the distillation head and was weighed to determine the mass of material in the flask. A measured amount of internal standard (dimethylsulfoxide) was added to the reaction flask and it was mixed well. The contents of the reaction flask were then transferred to a 50 mL centrifuge tube. The distillation head was washed with water and the washes were also used to wash the reactor pot. All the washes were combined in the 50 mL centrifuge tube, and solids were centrifuged to the bottom of the tube using the supernatant for analysis.

The distillate, reaction flask contents, and the washes were then analyzed by HPLC on a calibrated Biorad Aminex HPX-87H column using a refractive index detector. An aqueous 0.01 $NH_2SO_4$ isocratic mobile phase flowing at 0.6 mL/min through a column heated to 65° C. and a refractive index detector heated to 55° C. The detected amounts of xylose and furfural were recorded. Results for different solid acid catalysts are presented in Table 1.

TABLE 1

| Run | Original Catalyst Source | Catalyst Type or Zeolite Framework Type | Mole Ratio Si/Al in Catalyst | Mole Ratio (Al/Al + Si) in Catalyst | Surface Area ($m^2$/g) | Xylose Conversion (%) | Selectivity to Furfural (%) | Yield of Furfural (%) |
|---|---|---|---|---|---|---|---|---|
| 1.1 | CP814E | BEA | 12.5 | 0.074 | 680 | 99 | 74 | 73 |
| 1.2 | CP814C | BEA | 19 | 0.05 | 710 | 97 | 74 | 72 |
| 1.3 | CP811B-200 | BEA | 100 | 0.01 | — | 94 | 67 | 63 |
| 1.4 | Amberlyst™ 70 | polymer | — | — | — | 93 | 63 | 59 |
| 1.5 | CP811C-300 | BEA | 150 | 0.007 | 620 | 91 | 62 | 57 |
| 1.6 | CBV 720 | FAU | 15 | 0.063 | 780 | 89 | 57 | 51 |
| 1.7 | CBV 3020 | MFI | 15 | 0.063 | 405 | 92 | 55 | 51 |
| 1.8 | CBV 30A | MOR | 15 | 0.063 | 600 | 91 | 55 | 50 |
| 1.9 | CBV 780 | FAU | 40 | 0.024 | 780 | 90 | 55 | 49 |
| 1.10 | CBV 760 | FAU | 30 | 0.032 | 720 | 92 | 52 | 48 |

TABLE 1-continued

| Run | Original Catalyst Source | Catalyst Type or Zeolite Framework Type | Mole Ratio Si/Al in Catalyst | Mole Ratio (Al/Al + Si) in Catalyst | Surface Area (m²/g) | Xylose Conversion (%) | Selectivity to Furfural (%) | Yield of Furfural (%) |
|---|---|---|---|---|---|---|---|---|
| 1.11 | CBV 20A | MOR | 10 | 0.091 | 500 | 91 | 53 | 48 |
| 1.12 | CBV 712 | FAU | 6 | 0.143 | 730 | 87 | 47 | 41 |
| 1.13 | CBV 1502 | MFI | 75 | 0.013 | 420 | 86 | 46 | 40 |
| 1.14 | 13% Nafion/SiO$_2$ | polymer | — | — | — | 91 | 44 | 40 |
| 1.15 | CBV 2802 | MFI | 140 | 0.007 | 411 | 88 | 43 | 38 |
| 1.16 | CBV 5020 | MFI | 25 | 0.038 | 425 | 87 | 42 | 37 |
| 1.17 | CBV 500 | FAU | 260 | 0.278 | 750 | 84 | 29 | 24 |
| 1.18 | CBV 400 | FAU | 255 | 0.282 | 730 | 83 | 25 | 20 |

The catalysts that gave the highest yields in these experiments were the beta zeolites, particularly catalysts derived from calcinations of CP814C and CP814E. Amberlyst™ 70 also gave high yields and conversion.

Example 2

Furfural Production by a Continuous Process Using Solid Acid Catalyst

A 200 mL round-bottomed flask with a 29/26 joint was modified for the experiment. Three threaded joints were sealed to the flask. Two of these joints (Chemglass, Inc. PN CG-350-10) were capable of forming a compression seal with ⅛" (0.318 cm) outer diameter fluoropolymer tubing used in the process. and the third joint (Chemglass, Inc. PN CG-350-01) was used as an extra port that could be sealed with a septum and used when necessary. The modified flask was loaded with a fluoropolymer-coated magnetic stirring bar, 100 g of sulfolane, and 1.53 g of beta zeolite catalyst CP814E (Zeolyst) that was calcined for 8 h at 550° C. before use. The flask was connected to a distillation column (Chemglass, Inc. Lifescience Company Catalog No. CG1247-10) containing 150 g of 6 mm diameter glass beads held in place by a piece of folded fluoropolymer material. The distillation column was connected to a condenser that was chilled to about 15° C. with a recirculating chiller. The reaction flask was lowered into a tin/bismuth metal bath heated to 275° C. in order to generate an internal reaction temperature of approximately 175° C. One of the fluoropolymer tubes sealed in the compression joint had one end submerged in the hot reaction mixture. To the submerged end of this tube was connected a glass frit that acted as a filter to keep the solid acid catalyst in the reaction pot while still enabling the removal of the soluble reaction media. This tube was connected to a peristaltic pump (Masterflex PTFE pump head, PN 77390-00) which was removing the reaction mixture away from the reaction flask at approximately 0.5 mL/min; this was pumped through the other end of the tube into a small mixing chamber (Swagelok fitting, PN SS-200-3TFT) containing a small fluoropolymer-coated magnetic stirring bar. Also pumped into this mixing chamber was a 5 wt % aqueous xylose solution. This solution was placed on a balance and was weighed at the start of the reaction. Over the 12.9 h reaction window described here, 1593 g of the xylose solution (80 g of xylose) was pumped through the small mixing chamber using an HPLC pump (Gilson) at a rate of approximately 2 mL/min or a 4:1 dilution ratio relative to the reaction mixture, thereby initiating precipitation. A back pressure regulator set at 0.21 MPa was installed after the HPLC pump to maintain a constant flow of sugar solution into the small mixing chamber. After precipitation in the mixing chamber, the water/sulfolane/xylose solution containing suspended humins was transported through a switching valve and into a 102 mm stainless steel filter holder (made inhouse). The filter holder assembly contained a disc of 1 μm polypropylene filter media from a filter bag (Eaton Corporation, PO-1-PO2E-WW-30X) which was used to filter the solid formed after the mixing chamber. The clear filtrate from the filter assembly flowed into a 400 mL screw cap bottle (VWR, 16157-169) modified by the addition of two threaded joints (Chemglass, Inc. PN CG-350-01) and a GL-45 cap (Chemglass, Inc. PN CG-1158-20) containing three ports for ⅛" tubing. The bottle sat atop a magnetic stirring plate (IKA) in order to rotate a fluoropolymer-coated magnetic stirring bar contained in the bottom of the bottle. A pH electrode (Orion PN 911600) was inserted through one of the bottle joints and sealed with the compression cap and o-ring to the bottle. (This apparatus was referred to as the pH adjustment chamber, although in this experiment, no pH adjustment was made). The pH electrode was connected to a pH meter (Eutech Instruments, pH 200 Series). A ⅛" fluoropolymer tube submerged to the bottom of the pH adjustment chamber was connected to a valveless rotating and reciprocation pump (pump head was from Fluid Metering Inc., PN RH00 and the drive was from Scilog). The filtrate liquid was pulled from the pH adjustment chamber to the pump head and was then pushed through a ⅛" diameter fluoropolymer and into the reactor, just above the solvent level. The pump was set to deliver approximately 2.5 mL/min from the pH adjustment chamber into the reaction vessel. The total volume of the reaction mixture in the reactor was approximately 75 mL, making the reaction volume to total flow rate ratio equal to 30/min (meaning that the reaction volume was 30 times as great as the volume flowing into the reactor every minute). When the filtrate solution containing xylose, water and sulfolane entered the hot reaction flask, the xylose was converted to furfural and was distilled along with the water through a distillation column and was condensed.

The sulfolane and solid acid remained in the reaction flask. The distillate was collected and analyzed for furfural. The total amount of furfural collected in the 12.9 hour reaction window was 31.2 g corresponding to 60% furfural molar yield. The solids collected on the filtration assemblies were washed and dried. The total amount of washed and dried solid collected in 12.9 h was 9.8 g.

Comparative Example A

Using an analogous procedure as described in Example 1, the materials derived from S-115 (LA) and CBV 10A after calcination were tested as catalysts for production of furfural. The results are presented in Table 2.

TABLE 2

| Run | Catalyst Name | Catalyst Type | Mole ratio Si/Al in Catalyst | Mole ratio (Al/Al + Si) in Catalyst | Surface Area ($m^2/g$) | Xylose Conversion (%) | Selectivity to Furfural (%) | Yield of Furfural (%) |
|---|---|---|---|---|---|---|---|---|
| A.a | S-115 (LA) | MFI | 400 | 0.002 | 411 | 77 | 1 | 0 |
| A.b | CBV 10A | MOR | 5 | 0.167 | 425 | 15 | 0 | 0 |

The catalysts derived from S-115 (LA), a zeolite with very low aluminum content, and CBV 10A, a zeolite with sodium cations and few Bronsted acid sites, showed 0% yield of furfural in Run A and Run B. This demonstrated that zeolites with a low number of Brönsted acid sites, or low aluminum content (very high Si/Al ratio, greater than or equal to 400) were not good catalysts for furfural production from $C_5$ and/or $C_6$ sugars.

What is claimed is:

1. A process comprising:
   (a) providing a reactor comprising a distillation column disposed on top of a reaction vessel, wherein the reaction vessel contains a solid acid catalyst in a water-miscible organic solvent;
   (b) bringing an aqueous feedstock solution into contact with the solid acid catalyst and the water miscible organic solvent in the reaction vessel for a residence time sufficient to produce a mixture of water and furfural, wherein the aqueous feedstock solution comprises $C_5$ sugar, $C_6$ sugar or a mixture thereof, and wherein the contents of the reaction vessel are at a temperature in the range of 100-250° C. and a pressure in the range of 0.0001-0.21 MPa;
   (c) removing the mixture of water and furfural from the top of the distillation column; and
   (d) adding water or the aqueous feedstock solution to at least a portion of the contents of the reaction vessel comprising organic solvent, water, unreacted sugars and nonvolatile byproducts to precipitate water-insoluble byproducts and removing the precipitated water-insoluble byproducts.

2. The process according to claim 1, wherein the process is a continuous process further comprising:
   (e) adding at least one of water-miscible organic solvent or aqueous feedstock solution to the precipitate-free liquid obtained in step (d) and using it as the aqueous feedstock solution in step (b).

3. The continuous process according to claim 2 further comprising:
   (f) separating furfural from the removed mixture of water and furfural of step (c); and
   (g) using water of step (f) in making the aqueous feedstock solution of step (d).

4. The process according to claim 1 further comprising:
   (h) concentrating by evaporation at least a portion of the precipitate-free liquid obtained in step (d) and using it as the aqueous feedstock solution in step (b).

5. The process according to claim 1, wherein the water-miscible organic solvent is sulfolane, polyethylene glycol, isosorbide dimethyl ether, isosorbide, propylene carbonate, poly(ethylene glycol) dimethyl ether, adipic acid, diethylene glycol, 1,3-propanediol, glycerol, gamma-butyrolactone, 2-methyl-1-pyrrolidinone, gamma-valerolactone, or mixtures thereof.

6. The process according to claim 1 wherein the solid acid catalyst comprises a zeolite or a sulfonic-acid-functionalized polymer.

7. The process according to claim 6 wherein the solid acid catalyst is a medium or large pore, acidic, hydrophobic zeolite.

8. The process according to claim 7 wherein the zeolite comprises ZSM-5, faujasite, beta zeolite, Y zeolite, mordenite, or a combination of any of these.

9. The process according to claim 1 wherein the combined concentration of $C_5$ sugar and/or $C_6$ sugar in the aqueous feedstock solution is in the range of 1-90 weight percent based on the total weight of the aqueous feedstock solution.

10. The process according to claim 1 wherein the combined concentration of $C_5$ sugar and/or $C_6$ sugar in the aqueous feedstock solution is in the range of 4-35 weight percent based on the total weight of the aqueous feedstock solution.

11. The process according to claim 1 wherein the aqueous feedstock solution comprises xylose, glucose, or a mixture thereof.

12. A process comprising the steps of:
   a) providing a water-miscible organic solvent and a solid acid catalyst in a reaction vessel, wherein the boiling point of the solvent is higher than about 100° C.;
   b) providing an aqueous feedstock solution comprising: at least one $C_5$ sugar, at least one $C_6$ sugar, or a mixture of at least one $C_5$ sugar and at least one $C_6$ sugar;
   c) adding the feedstock solution to the reaction vessel to form a reaction mixture wherein
      i) the temperature of the reaction mixture is between about 100° C. and about 250° C.,
      ii) the reaction mixture pressure is between 0 MPa and about 0.21 MPa, and
      iii) the feedstock, organic solvent, and catalyst are in contact for a time sufficient to effect a reaction to produce furfural and water;
   d) removing vapors of furfural and water from the reaction mixture via reflux through a multistage distillation column;
   e) condensing and collecting a solution of furfural and water; and f) recovering the furfural from the solution of furfural and water collected in step e).

13. The process of claim 12 wherein the contents of the reaction vessel are heated to a temperature between about 100° C. and about 250° C. before step c).

14. The process of claim 12 further comprising the steps of:
g) separating the remaining contents, or a portion thereof, of the reaction vessel from the solid acid catalyst;
h) diluting the remaining contents of the reaction vessel, or a portion thereof, in a mixing chamber with water or with an aqueous feedstock solution comprising: at least one $C_5$ sugar, at least one $C_6$ sugar, or a mixture of at least one $C_5$ sugar and at least one $C_6$ sugar, thereby precipitating water-insoluble byproducts;
i) removing the byproducts precipitated in step h), and
j) feeding the solution remaining after step i) back to the reaction vessel.

15. The process according to claim 14, further comprising adding water or an aqueous feedstock solution to the reaction vessel contents remaining after step d), thereby precipitating water-insoluble byproducts; and removing the precipitated byproducts.

* * * * *